US012708720B2

(12) United States Patent
Carlsson

(10) Patent No.: US 12,708,720 B2
(45) Date of Patent: Aug. 18, 2026

(54) NEEDLE CUTTING DEVICE FOR CUTTING AN INJECTOR NEEDLE

(71) Applicant: SHL Medical AG, Zug (CH)

(72) Inventor: Daniel Carlsson, Nacka Strand (SE)

(73) Assignee: SHL Medical AG, Zug (CH)

(*) Notice: Subject to any disclaimer, the term of this patent is extended or adjusted under 35 U.S.C. 154(b) by 377 days.

(21) Appl. No.: 18/681,691

(22) PCT Filed: Jul. 27, 2022

(86) PCT No.: PCT/EP2022/071097
§ 371 (c)(1),
(2) Date: Feb. 6, 2024

(87) PCT Pub. No.: WO2023/016813
PCT Pub. Date: Feb. 16, 2023

(65) Prior Publication Data

US 2024/0342392 A1 Oct. 17, 2024

(30) Foreign Application Priority Data

Aug. 10, 2021 (EP) ..................................... 21190586

(51) Int. Cl.
*A61M 5/32* (2006.01)

(52) U.S. Cl.
CPC ... *A61M 5/3278* (2013.01); *A61M 2005/3282* (2013.01)

(58) Field of Classification Search
CPC .................... A61M 5/3278; A61M 2005/3282
See application file for complete search history.

(56) References Cited

U.S. PATENT DOCUMENTS 3,736,824 A 6/1973 Dunnican
4,332,323 A 6/1982 Reenstiema
(Continued)

FOREIGN PATENT DOCUMENTS

CN 110464477 A 11/2019
EP 3581218 A1 12/2019
(Continued)

OTHER PUBLICATIONS

International Search Report and Written Opinion for corresponding PCT application No. PCT/EP2022/071097 dated Sep. 19, 2022.

*Primary Examiner* — Dung T Ulsh
(74) *Attorney, Agent, or Firm* — McDonnell Boehnen Hulbert & Berghoff LLP

(57) ABSTRACT

The present disclosure provides a needle cutting device for cutting an injector needle. The needle cutting device includes a housing extending along a longitudinal axis between a first open end and a second end. The needle cutting device also includes a cutter assembly aligned with the housing along the longitudinal axis, wherein the cutter assembly comprises a blade and a cutter body. The housing comprises a wall that defines a cavity, the cavity extending between the first open end of the housing and the second end of the housing. A blade support portion of the cutter body is wider than the cavity, so that when the cutter body is moved into the cavity, the wall of the housing pushes the blade support portion in the radial direction relative to the longitudinal axis so that the blade is moved towards the longitudinal axis.

15 Claims, 8 Drawing Sheets

(56) References Cited

U.S. PATENT DOCUMENTS

| | | | | |
|---|---|---|---|---|
| 6,545,242 | B1 | 4/2003 | Butler | |
| 10,238,811 | B2 | 3/2019 | Limaye | |
| 10,524,873 | B2 | 1/2020 | Sall | |
| 10,751,146 | B2 | 8/2020 | Joyce | |
| 10,943,685 | B2 | 3/2021 | Gylleby | |
| 10,987,100 | B2 | 4/2021 | Gorek | |
| 2004/0244202 | A1 * | 12/2004 | Bull .................... | A61M 5/3278 30/124 |
| 2020/0090797 | A1 | 3/2020 | Gylleby | |

FOREIGN PATENT DOCUMENTS

| | | | |
|---|---|---|---|
| EP | 2913078 | A1 | 1/2020 |
| KR | 200472067 | Y1 | 4/2014 |
| WO | 2016198428 | A1 | 12/2016 |
| WO | 2018104113 | A1 | 6/2018 |
| WO | 2020263249 | A1 | 12/2020 |
| WO | 2021033825 | A1 | 2/2021 |

* cited by examiner

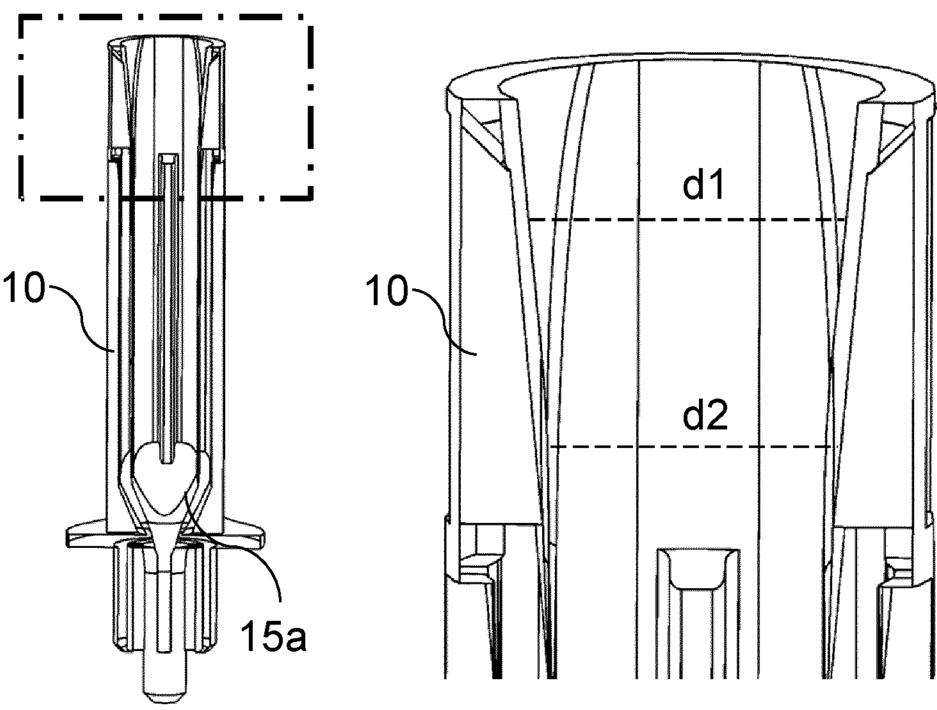
Fig. 2A
Fig. 2B
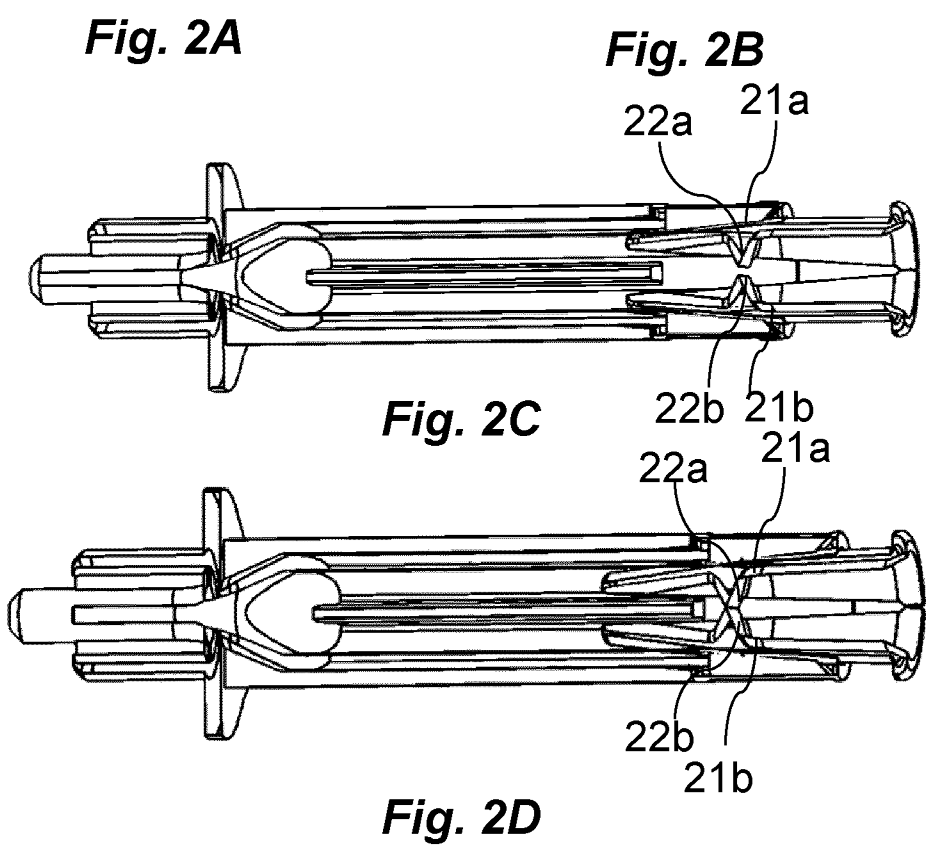
Fig. 2C
Fig. 2D

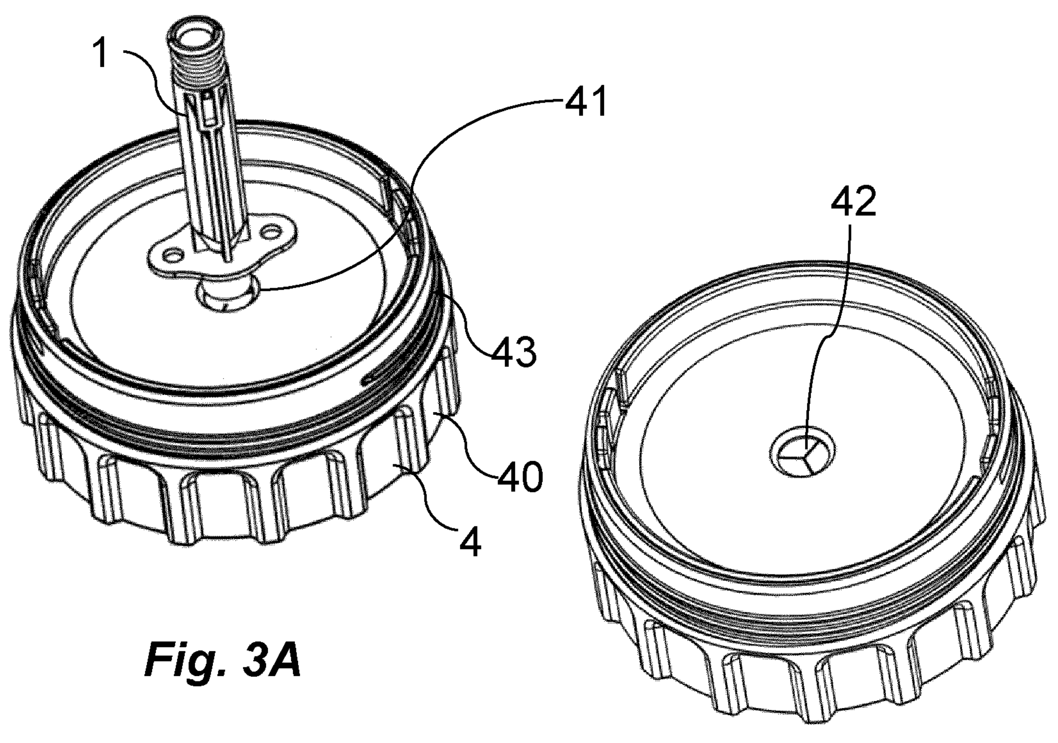
Fig. 3A
Fig. 3B
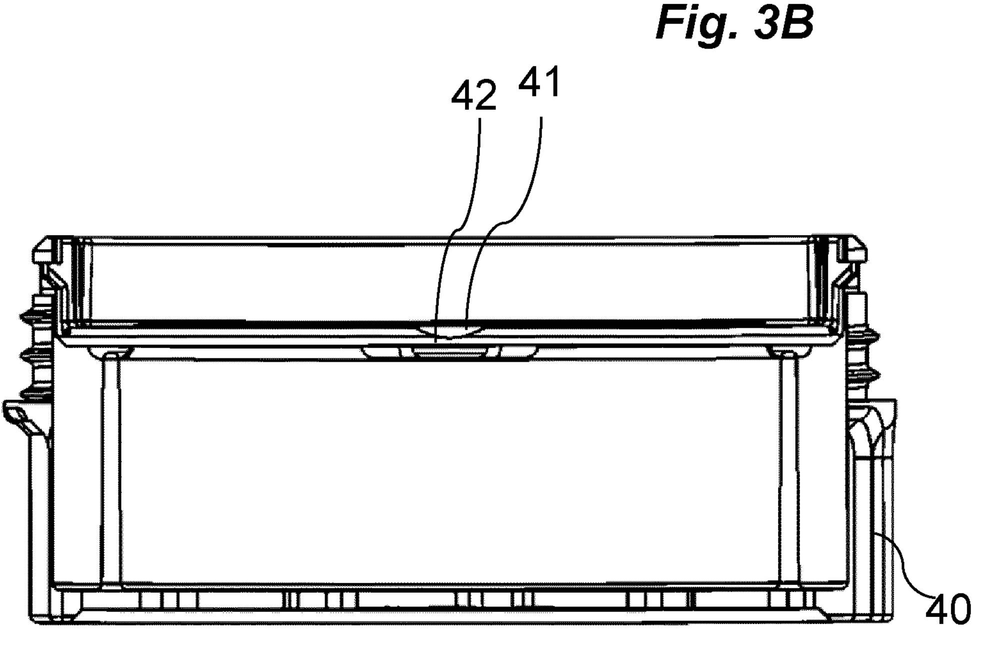
Fig. 3C

NEEDLE CUTTING DEVICE FOR CUTTING AN INJECTOR NEEDLE

CROSS-REFERENCE TO RELATED APPLICATIONS

The present application is a U.S. National Phase Application pursuant to 35 U.S.C. § 371 of International Application No. PCT/EP2022/071097 filed Jul. 27, 2022, which claims priority to European Patent Application No. 21190586.4 filed Aug. 10, 2021. The entire disclosure contents of these applications are herewith incorporated by reference into the present application.

TECHNICAL FIELD

The present disclosure generally relates to a needle cutting device for cutting an injector needle, and particularly to a needle cutting device comprising a cutter assembly with a cutter body comprising a blade support portion.

BACKGROUND

Needle stick injuries resulting from accidental contact with an injector needle pose a serious health risk, particularly if the needle has been in contact with blood. Removing the needle from the injector and safely storing the cut needles can reduce the risk of such injuries.

It has been appreciated that solutions for providing a device for cutting needles off injectors that is easy to use by users without any professional training would be beneficial.

SUMMARY

The invention is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", or "circumferentially" refer to a circumference or a circumferential direction relative to an axis, typically a central axis extending in the direction of the longest extension of the device and/or component. Similarly, "radial" or "radially" refer to a direction extending radially relative to the axis, and "rotation", "rotational" and "rotationally" refer to rotation relative to the axis.

There is hence provided a needle cutting device for cutting an injector needle, the needle cutting device comprising: a housing extending along a longitudinal axis between a first open end and a second end; a cutter assembly aligned with the housing along the longitudinal axis, the cutter assembly comprises a blade and a cutter body; the cutter body comprises a blade support portion; the blade support portion is movable in a radial direction relative to the longitudinal axis; and the blade extends from the blade support portion of the cutter body towards the longitudinal axis; and the housing comprises a wall that defines a cavity, the cavity extending between the first open end of the housing and the second end of the housing; the blade support portion of the cutter body is wider than the cavity, so that when the cutter body is moved into the cavity, the wall of the housing pushes the blade support portion in the radial direction relative to the longitudinal axis so that the blade is moved towards the longitudinal axis.

Preferably, according to another embodiment, the cutter assembly is movable relative to the housing along the longitudinal axis between a first position where the cutter body is positioned out of the cavity and a second position where the cutter body is positioned in the cavity.

Preferably, according to another embodiment, the cutter assembly comprises a blade receiver; and the blade receiver is arranged on an inner surface of the cutter body and is opposite to the blade with respect to the longitudinal axis.

Preferably, according to another embodiment, the blade receiver is arranged on a movable portion of the cutter body; the movable portion is movable in the radial direction relative to the longitudinal axis and opposite to the blade support portion, so that when the cutter body is moved into the cavity, the wall that forms the cavity pushes both the blade support portion and the movable portion towards the longitudinal axis, so that the blade and the blade receiver are moved into contact with one another or so that the blade and the blade receiver overlap one another in the direction of the longitudinal axis.

Preferably, according to another embodiment, the blade receiver is a wall.

Preferably, according to another embodiment, the blade receiver is a second blade.

Preferably, according to another embodiment, the cutter assembly is at least partially arranged within the housing.

Preferably, according to another embodiment, the housing is tubular.

Preferably, according to another embodiment, the second end of the housing is an open end.

Preferably, according to another embodiment, the blade support portion of the cutter body comprises a protrusion extending from a surface of the blade support portion, the surface faces away from the longitudinal axis.

Preferably, according to another embodiment, a cut-out/recess is arranged in a wall of the housing, the cut-out/recess extending in a direction transverse to the longitudinal axis.

Preferably, according to another embodiment, when the cutter assembly is in the first position, the protrusion of the blade support portion of the cutter body is fully positioned within the cut-out/recess; and when the cutter assembly is in the second position, at least a part of the protrusion of the blade support portion of the cutter body is positioned within the cavity of the housing.

Preferably, according to another embodiment, the blade support portion of the cutter body comprises two arms extending from the surface of the cutter body in the direction of the longitudinal axis towards the second end of the housing.

Preferably, according to another embodiment, the blade extends from one of the two arms of the blade support portion; and the blade receiver extends from the other one of the two arms of the blade support portion towards the longitudinal axis.

Preferably, according to another embodiment, the cutter body comprises a support surface facing towards the second end of the housing; the housing comprises a counter support surface facing towards the first end of the housing; and the needle cutting device comprises a biasing member adjacent to the support surface of the cutter body at one end, and adjacent to the counter surface of the housing at the other end.

Preferably, according to another embodiment, the needle cutting device comprises a container attached to the second end of the housing; the container comprises an opening coaxial relative to the housing.

Preferably, according to another embodiment, the container is releasably attached to the second end of the housing.

Preferably, according to another embodiment, the container comprises a resilient valve arranged at the opening of the container; the second end of the housing is configured to at least partially protrude through the resilient valve when the container is attached to the housing.

Preferably, according to another embodiment, the needle cutting device comprises an outer shell attached to the housing; the outer shell extends along a longitudinal axis between a first end and a second end; the outer shell comprises a shell body formed between the first end and the second end, a first opening at the first end, and a second opening at the second end; the shell body of the outer shell is configured to at least partially surround the housing; and wherein an inner surface of the shell body of the outer shell is spaced apart from an outer surface of the housing.

Preferably, according to another embodiment, the needle cutting device comprises a set of electronics arranged within the shell body of the outer shell; the set of electronics comprises a switch configured to be switched on upon detection of movement relative to the switch in a space between the inner surface of the shell body of the outer shell and the outer surface of the housing.

Preferably, according to another embodiment, the switch comprises a flipping arm that extends into the space between the inner surface of the shell body of the outer shell and the outer surface of the housing.

Preferably, according to another embodiment, the switch comprises an emitter and a receiver; the emitter is configured to emit a light beam or an acoustic wave towards the space between the inner surface of the shell body of the outer shell and the outer surface of the housing; and the receiver is configured to receive a reflected light or acoustic signal and to switch on the switch in response to a change of receiving the reflected light or acoustic signal.

Preferably, according to another embodiment, the needle cutting device comprises a partition positioned between the set of electronics and the housing; an aperture is arranged in the partition and is lined up with the switch of the set of electronics.

Preferably, according to another embodiment, the set of electronics is configured to perform, when the switch is switched on, at least one action of: providing a visual, an audible, and/or a tactile indication; recording data; sensing a physical property related to an injector; reading a data from a data medium; and transmitting data.

Preferably, according to another embodiment, the housing is indirectly attached to the container through an attachment between the outer shell and the container.

Preferably, according to another embodiment, the housing is sized to fit into a needle guard of an injector.

Another aspect of the present disclosure provides a method of cutting a needle, the method comprising the steps of: providing an injector with a needle guard surrounding a needle; providing a needle cutting device with a housing and a cutting assembly, wherein the cutting assembly comprises a cutter body defining a passage and a blade extending towards the passage, and wherein the cutting assembly is movably arranged along a longitudinal axis within the housing so that the cutting assembly can move relative to the housing between an uncut position where the blade is spaced apart from a center of the passage and a cut position where the blade extends beyond the center of the passage; inserting the housing of the needle cutting device into the needle guard of the injector; and cutting the needle by moving the cutting assembly relative to the housing from the uncut position to the cut position.

Preferably, according to another embodiment, the step of moving the cutting assembly relative to the housing comprises a step of moving the injector relative to the housing along the longitudinal axis.

Preferably, according to another embodiment, the injector is an autoinjector, an insulin pen, and a safety syringe.

Preferably, according to another embodiment, the needle guard of the injector can be a user-detachable needle guard or a non-detachable needle guard for an end-user.

Generally, all terms used in the claims are to be interpreted according to their ordinary meaning in the technical field, unless explicitly defined otherwise herein. All references to "a/an/the element, apparatus, component, means, etc." are to be interpreted openly as referring to at least one instance of the element, apparatus, component, means, etc., unless explicitly stated otherwise.

BRIEF DESCRIPTION OF THE DRAWINGS

Embodiments of the inventive concept will now be described, by way of example only, with reference to the accompanying drawings, in which:

FIGS. 2A-2B schematically show cross-section views of a housing of the needle cutting device of FIGS. 1A-1B.

FIGS. 2C-2D schematically show cross-section views of the needle cutting device of FIGS. 1A-1B.

FIGS. 3A-3B schematically show perspective views of a container of the needle cutting device of the present disclosure.

FIG. 3C schematically shows a cross-section view of the container of FIGS. 3A-3B.

DETAILED DESCRIPTION

Figures 1A, 1B, 1C, 1D:
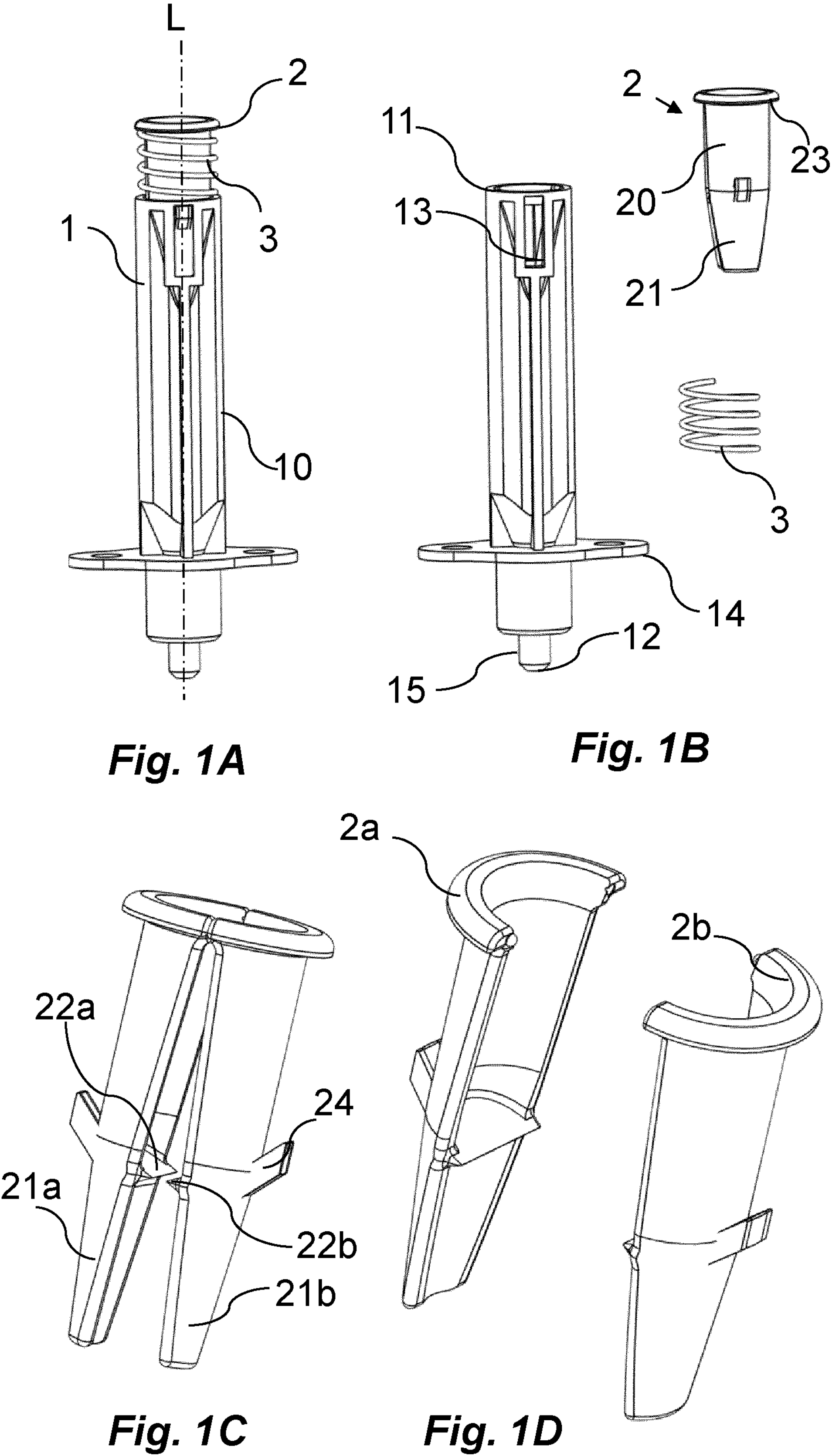
FIGS. 1A-B schematically show side views of a needle cutting device of the present disclosure.
FIGS. 1C-D schematically show perspective views of a cutter assembly of the needle cutting device of FIGS. 1A-1B.

FIGS. 1-8D illustrate a needle cutting device for cutting an injector needle. The needle cutting device comprises a housing 1 and a cutter assembly 2. The housing 1 extends along a longitudinal axis L between a first open end 11 and a second end 12. The cutter assembly 2 is aligned with the housing 1 along the longitudinal axis L. In one example, the cutter assembly is at least partially arranged within the housing 1. In one example, the second end 12 can be an open end.

The cutter assembly 2 comprises a blade 22*a*, 22*b* and a cutter body 20. The cutter body 20 defines a passage inside the cutter body for receiving a needle. The cutter body 20 comprises a blade support portion 21. The blade support portion 21 is movable in a radial direction relative to the longitudinal axis L.

The cutter assembly 2 is movable relative to the housing 1 along the longitudinal axis L between a first position where the cutter body 20 is positioned out of the cavity and a second position where the cutter body 20 is positioned in the cavity.

The blade support portion 21 is configured to be moved by the housing 1 when the cutter assembly 2 moves from the first portion (uncut position) to the second position (cut position), so that the blade can be therefore moved towards the longitudinal axis L for cutting the needle that is received within the passage. The housing 1 comprises a wall that defines a cavity extending between the first open end 11 of the housing 1 and the second end 12 of the housing 1. The blade support portion 21 of the cutter body 20 is wider than the cavity, so that when the cutter body 20 is moved into the cavity, the wall of the housing 1 pushes the blade support portion 21 in the radial direction relative to the longitudinal axis L, so that the blade 22*a*, 22*b* is moved towards the longitudinal axis L.

In another example, the cutter assembly comprises a blade receiver. The blade receiver is arranged on an inner surface of the cutter body and is opposite to the blade with respect to the longitudinal axis L. The needle that is received within the passage can be cut by a single blade, e.g. slashed, or can be cut between the blade and the blade receiver.

The blade is configured to be in contact with or overlap with the blade receiver when the cutting assembly is in the second position. The blade receiver can be a wall or a second blade, so that the needle can be cut between the blade and either the wall or the second blade. The housing can be formed in any suitable shape. For example, the housing can be tubular.

In another example, the blade receiver is arranged on a movable portion 21*b* of the cutter body 20. The movable portion 21*b* is movable in the radial direction relative to the longitudinal axis L and opposite to the blade support portion 21*a*, so that when the cutter body 20 is moved into the cavity, the wall that forms the cavity pushes both the blade support portion 21*a* and the movable portion 21*b* in the radial direction relative to the longitudinal axis L, thereby the blade and the blade receiver are moved in contact with or overlap with each other.

In one example as shown in FIGS. 1A-1B, the housing 1 comprises a tubular wall 10 extending between the first open end 11 and the second end 12 in the direction of the longitudinal axis L. Optionally, a cut-out/recess 13 is arranged a wall of the housing 1. In a preferred example, the cut-out/recess 13 is arranged at the tubular wall 10 of the housing 1 in the direction transverse to the longitudinal axis L. Further, the housing 1 optionally comprises a fastener 14. In one example, the tubular wall 10 of the housing 1 comprises a narrow section 15 arranged at the second end 12 of the housing 1. The narrow section 15 typically has a diameter smaller than a diameter of any other parts of the tubular wall 10.

In one example, as shown in FIGS. 1C-1D, the cutter assembly comprises the cutter body 20 defining the passage. The passage and the housing 1 are coaxial. The cutter body 20 of the cutter assembly 2 comprises the blade support portion 21 extending from a surface of cutter body 20 in the direction of the longitudinal axis L towards the second end 12 of the housing 1. In this example, the blade receiver is a second blade. In other word, the cutter body 20, in this example, comprises two blades 22*a*, 22*b* extending from the blade support portion 21 of the cutter body 20 towards the longitudinal axis L and facing towards one another. In this example, the movable portion 21*b* of the cutter body 20 is also a blade support portion. In one example, the blade support portion 21 and the movable portion of the blade receiver comprises two arms 21*a*, 21*b* extending from the surface of the cutter body in the direction of the longitudinal axis L towards the second end 12 of the housing 1. In this example, each of the two arms 21*a*, 21*b* comprises one of the two blades 22*a*, 22*b* arranged on an inner surface of each two arms 21*a*, 21*b*, as shown in FIG. 1C-1D. In one example, the two arms 21*a*, 21*b* are flexible. In another example, the two arms are pivotally connected to the cutter body, so that the two arms can pivot towards the longitudinal axis L. In another example, the blade support portion of the cutter body comprises a resilient cylindrical body. In this example, the two blades are arranged on an inner surface of the resilient cylindrical body. The needle cutting device optionally comprises a biasing member 3. In this example, the cutter assembly 2 comprises a support surface 23 facing towards the second end 12 of the housing 1; and the housing comprises a counter support surface facing towards the first open end 11 of the housing 1. In a preferred example, the counter support surface of the housing 1 is arranged at the first open end 11 of the housing. The biasing member 3 is adjacent to the support surface 23 of the cutter body 20 at one end, and adjacent to the counter surface of the housing 1 at the other end, as shown in FIG. 1A. Alternatively, instead of the biasing member 3, the needle cutting device comprises a pair of magnets, e.g. permanent magnet material or an electromagnetic arrangement; one of the magnets is arranged around the first open end of the housing, and the other of the magnets is arranged around the cutter body. The two magnets are configured to repel one another by arranging the same poles of the two magnets facing towards one another (N-N or S-S). In this example, supported by the magnetic force, the cutter body can be either floating on the first open end of the housing or partially within the housing, but floating on the cavity when the cutter assembly is in the first position. Once the magnetic force is overcome, e.g. by a user's hand, the cutter body can be pushed into the cavity, so that the cutter assembly is moved into the second position. When the user's hand is removed from the cutter body, the magnetic force moves the cutter assembly back to the first position.

The cutter assembly 2 is axially movable relative to the housing 1 between a first position, as shown in FIG. 2C, and a second portion where the housing 1 is engaged with an outer portion of the blade support portion 21 of the cutter body 20 so that the two blades 22*a*, 22*b* are moved to contact with or overlapped with one another together with the blade support portion of the cutter body, as shown in FIG. 2D.

In one example, the housing 1 comprises a first portion having a first diameter d1, and a second portion having a second diameter d2 smaller than the first diameter d1, as shown in FIG. 2B. In this example, the cavity is the second portion of the housing 1. It should be noted that, when the tubular wall 10 of the housing 1 comprises the narrow section 15, the second portion can either be the narrow section 15 or can be a portion other than the narrow section 15. When the cutter assembly 2 is in the first position, the outer portion of the blade support portion 21 is positioned within the first portion of the housing 1; and when the cutter assembly 2 is in the second position, the outer portion of the blade support portion is positioned within the second portion of the housing 1. In this example, the cutter body 20 has a diameter that is smaller than or equal to the first diameter d1 of the first portion of the housing 1, and is greater than the second diameter d2 of the second portion of the housing 1. In this example, the portion of the cutter body 20 with the diameter defines the outer portion of the blade support portion 21. In another example, the cutter assembly 2 comprises a protrusion 24 extending from a surface of the blade support portion 21; the surface faces away from the longitudinal axis. In this example, the protrusion 24 comprises the outer portion of the blade support portion 22 of the cutter body 20. In this example, the housing 1 can be arranged with the two portions with two different diameters d1, d2, as mentioned above and/or with the cut-out/recess 13 arranged on the wall of the housing 1. In an example where the housing 1 comprises the first portion having a first diameter d1 and a second portion having the second diameter d2 smaller than the first diameter d1, when the cutter body is in the first position, the protrusion 24 is adjacent to the first portion of the housing; and when the cutter body is in the second position, the protrusion 24 is adjacent to the second portion of the housing 1. In an example where the cut-out/recess 13 arranged on the wall of the housing 1, the protrusion 24 of the blade support portion 21 of the cutter body 20 is fully positioned within the cut-out/recess 13; and when the cutter body is in the second position, at least a part of the protrusion of the blade support portion of the cutter body is positioned within the cavity of the housing. In a preferred example, when the cutter body 20 is in the first position, a distance between two blades 22*a*, 22*b* measured in a direction transverse to the longitudinal axis L is greater than a diameter of a needle, e.g. an 18-gauge needle, and is smaller than a diameter of a syringe nozzle.

Therefore, when the cutter assembly 2 is in the second position, the two blades 22*a*, 22*b* move to contact with or overlap with one another together with the blade support portion of the cutter body due to the resiliency/flexibility of the blade support portion 21 or the pivoting of the two arms 21*a*, 21*b* being squeezed by the engagement between the housing 1 and the outer portion of the blade support portion 22.

In one example, the cutter assembly 2 is manually moved by an end-user from the first position to the second position. The end-user can either directly move the cutter assembly 2 by hand or indirectly move the cutter assembly by the injector or any other suitable tool. In an example where the cutter assembly 2 comprises the biasing member 3, the biasing member 3 is configured to move the cutter assembly 2 axially relative to the housing 1 from the second position to the first position, so that the end-user does not need to manually move the cutter assembly 2 from the second position to the first position.

In a preferred example, the housing 1 is sized to fit into a needle guard of the injector. In this example, the needle cutting device is suitable for use with injectors with needle guards, e.g. auto-injectors or safety syringes, and with the injectors without needle guards, e.g. syringes. In a preferred example, the housing 1 has a diameter generally the same as a diameter of a rigid needle shield (RNS), e.g. 8 mm-8.5 mm. The RNS is typically a cover that tightly surrounds a rubber needle cap of a syringe. Therefore, the diameter of the RNS can only vary within a specific range in accordance with the diameter of the rubber needle cap. The dimension of needle guards of different injectors may be different, but most of the needle guards are capable of letting the RNS pass for RNS removal before use of the injector. In this example, the housing 1 has a diameter generally the same as a diameter of a rigid needle shield (RNS), and can therefore fit into the needle guards of most injectors.

The needle cutting device of the present disclosure can be operated with the following steps: providing an injector with a needle guard surrounding a needle; providing the needle cutting device; inserting the housing of the needle cutting device into the needle guard of the injector; positioning the needle into the passage; and cutting the needle by moving the cutting assembly relative to the housing from the uncut position to the cut position.

In another example, the needle cutting device comprises a container 4, as shown in FIGS. 3A-C. The container 4 comprises a container body 40 that has an interior space for containing the cut needles from injectors. The container body 40 can be formed in any suitable shape. The container 4 is configured to be attached to the second end 12 of the housing 1. In a preferred example, the container 4 is configured to be releasably be attached to the second end of the housing. The container can be directly or indirectly attached to the housing 1. For example, the container 4 comprises a fastener configured to attach the container 4 to the housing 1 via another component, or to attach the container 4 to the housing 1 directly.

Figures 4, 5A, 5B, 5C:
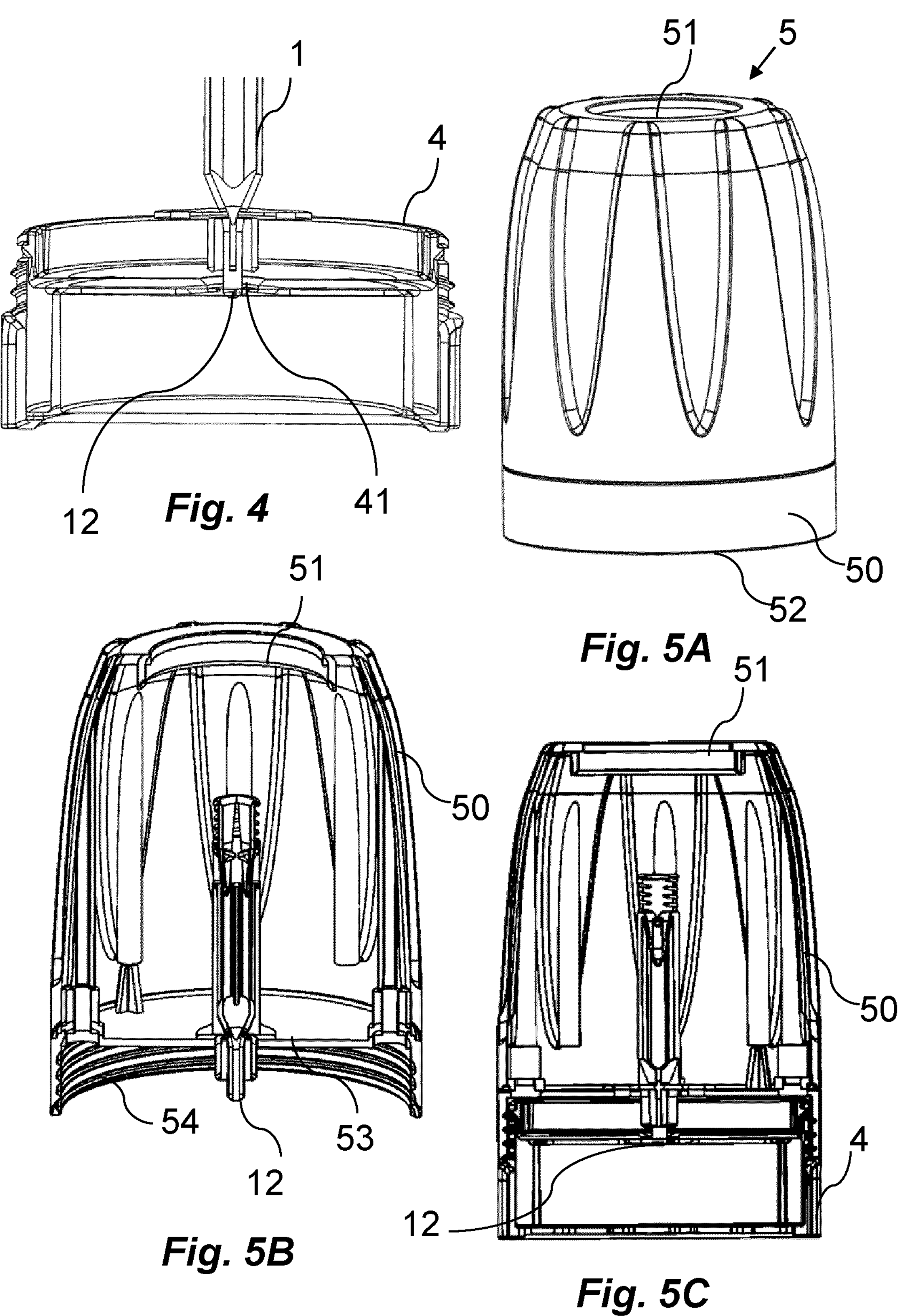
FIG. 4 schematically shows a cross-section view of the container of FIGS. 3A-3B with the housing of FIGS. 2A-2B.
FIG. 5A schematically show a side view of an outer shell of the needle cutting device of the present disclosure.
FIG. 5B schematically show a cross-section view of the outer shell of FIG. 5A with the housing of FIGS. 2A-2B and the cutter assembly of FIGS. 1C-1D.
FIG. 5C schematically show a cross-section view of the outer shell of FIG. 5A with the container of FIGS. 3A-3B, the housing of FIGS. 2A-2B, and the cutter assembly of FIGS. 1C-1D.
Figures 6A, 6B, 6C, 6D:
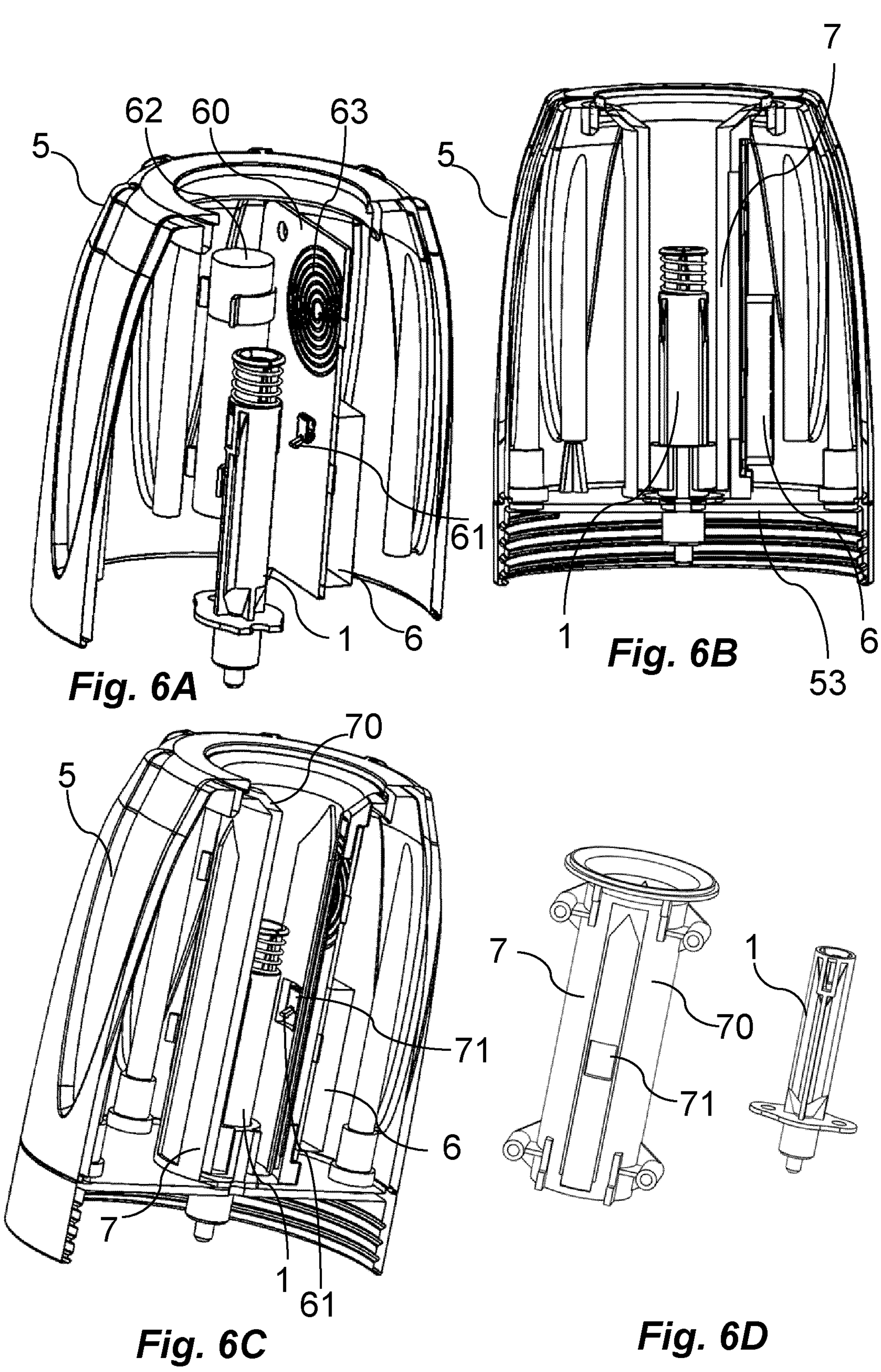
FIG. 6A schematically show a perspective views of a set of electronics of the needle cutting device arranged with the outer shell of FIG. 5A and the housing of FIGS. 2A-2B.
FIGS. 6B-6D schematically show cross-section views and a perspective view of a partition of the needle cutting device arranged between the housing of FIGS. 2A-2B and the set of electronics of FIG. 6A.
Figures 7A, 7B:
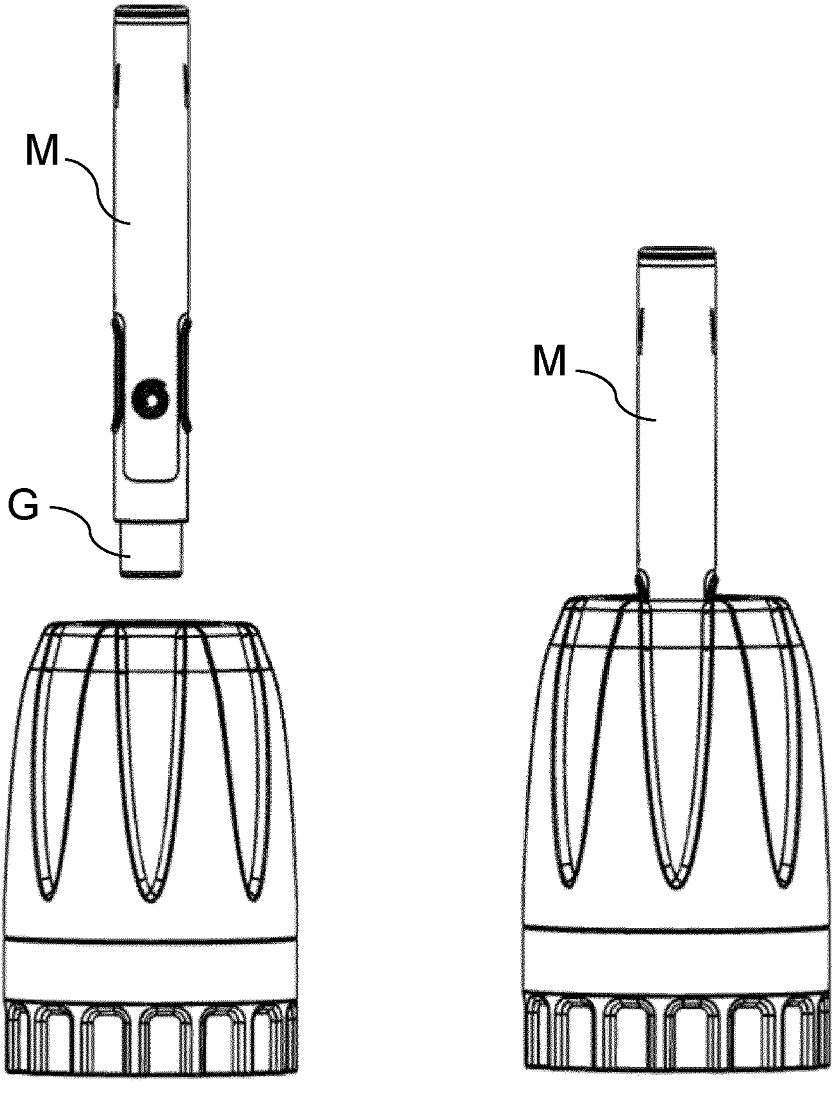
FIGS. 7A-7B schematically show side views of the needle cutting device of the present disclosure to be used with an injector comprising a needle guard.
Figure 7C:
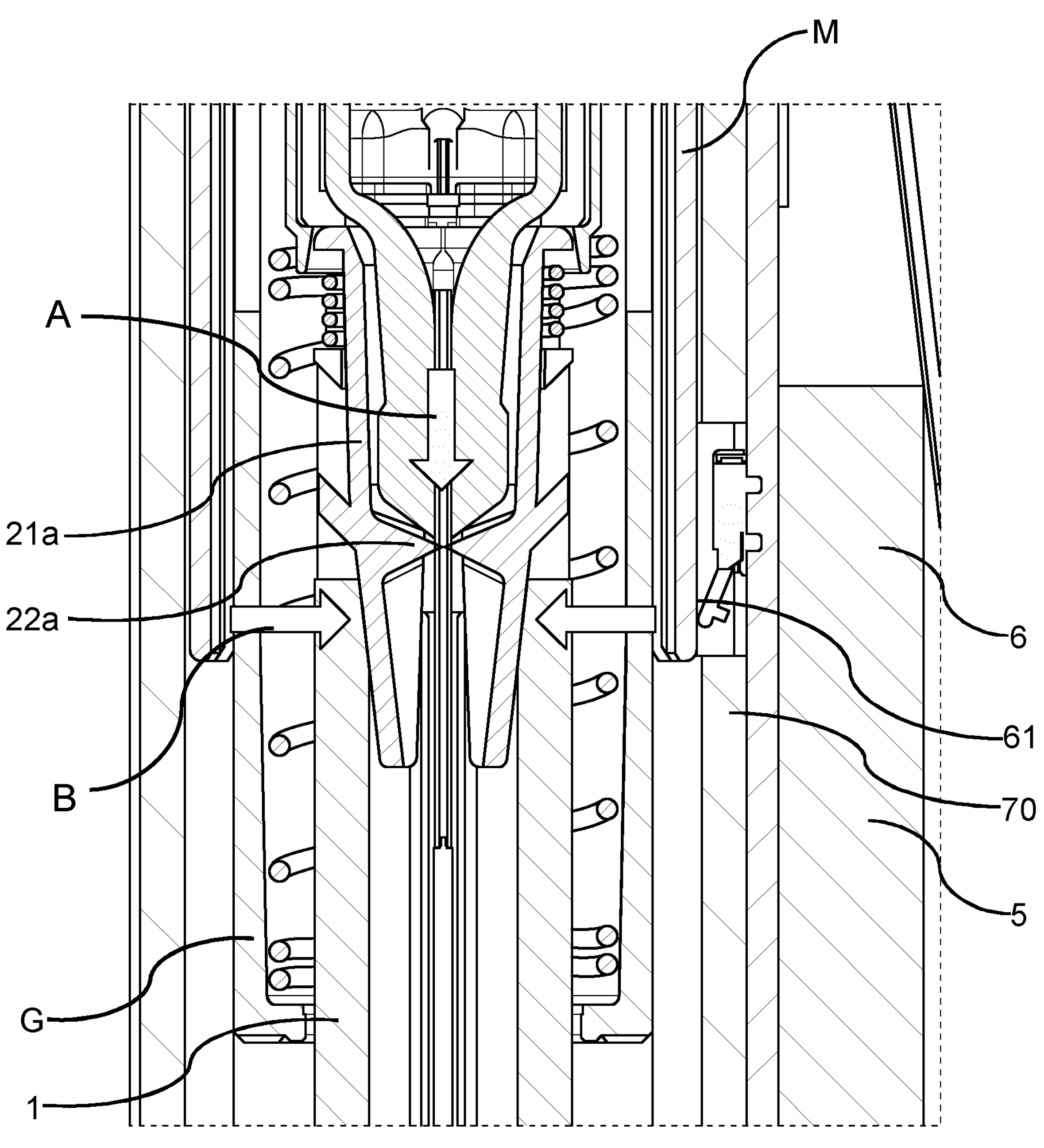
FIG. 7C schematically shows a cross-section view of the needle cutting device of the present disclosure to be used with the injector of FIG. 6A.
Figures 8A, 8B, 8C, 8D:
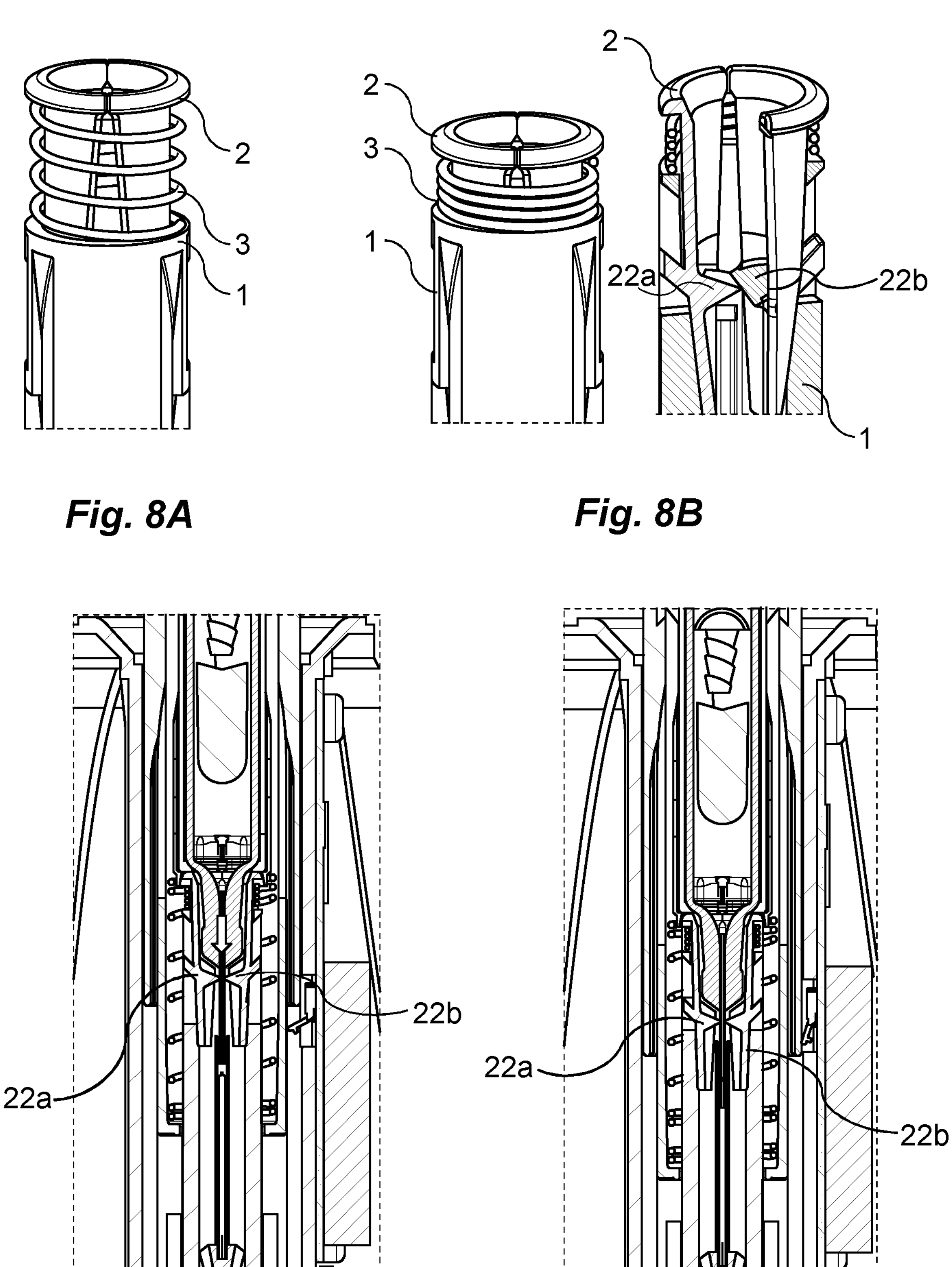
FIGS. 8A-8B schematically show perspective views of a biasing member of the needle cutting device of the present disclosure with the cutter assembly of FIGS. 1C-1D.
FIGS. 8C-8D schematically show cross-section views of the biasing member of FIGS. 8C-8D in different operation steps.

The container 4 comprises an opening 41. When the container is attached to the second end 12 of the housing 1, the opening 41 of the container 4 and the housing 1 are coaxial. Therefore, once a needle of an injector has been cut, the needle can be stored in the interior space of the container 4. In a preferred example, the container 4 comprises a resilient valve 42 arranged at the opening 41 of the container 4. The second end 12 of the housing 1 is configured to at least partially protrude through the resilient valve 42 when the container 4 is attached to the housing 1, as shown in FIG. 4. In one example, the resilient valve 42 can be made of a thermoplastic elastomer (TPE). When the second end 12 of the housing 1 protrudes through the resilient valve 42, the cut needles can enter into the interior space of the container 4 through the second end 12 of the housing 1. When the second end 12 of the housing 1 is not protruding through the resilient valve 42, for example because the container 4 has been detached from the housing 1, the resilient valve 42 is configured to close the opening 41 of the container 4, so that the contained needles will not fall out from the interior space of the container 4.

In another example, as shown in FIGS. 5A-5C, the needle cutting device comprises an outer shell attached to the housing 1. The outer shell 5 extends along a longitudinal axis between a first end and a second end. The outer shell comprises a shell body 50 formed between the first end and the second end. The outer shell 5 comprises a first opening 51 at the first end and a second opening 52 at the second end. In a preferred example, the longitudinal axis of the outer shell 5 is the same as the longitudinal axis of the housing 1 when the outer shell 5 is assembled with the housing 1, meaning that when the outer shell 5 is assembled with the housing 1, the first opening 51 of the outer shell 5 and the second opening of the outer shell 5 are coaxial, the first open end 11 of the housing 1 and the second end 12 of the housing 1 are coaxial as well. The shell body 50 of the outer shell is configured to at least partially surround the housing. An inner surface of the shell body 50 of the outer shell 5 is spaced away from an outer surface of the housing 1.

The outer shell optionally comprises a shell base 53 and a shell fastener 54. In a preferred example, the housing 1 is indirectly attached to the container 4 through an attachment between the outer shell 5 and the container 4. In this example, the fastener 14 of the housing 1 is configured to fix onto the shell base 53; and the shell fastener 54 is configured to fix to the fastener 43 of the container 4, e.g. by a screw or bayonet attachment. In this example, the container 4 is releasably fixed to the housing 1 indirectly through the outer shell 5.

The space between the inner surface of the shell body 50 and the outer surface of the housing 1 is configured to receive one or more components. For example, the needle cutting device comprises a set of electronics 6, as shown in FIGS. 6A-6D, arranged within the shell body 50 of the outer shell 5. In a preferred example, the set of electronics is arranged on a printed circuit board (PCB) 60 In a preferred example, the set of electronics 6 comprises a switch 61 configured to be switched on upon a detection of movement relative to the switch. Therefore, when an object moves relative to the switch 61 in the space between the inner surface of the shell body 50 of the outer shell 5 and the outer surface of the housing 1.

The switch 61 is configured to be switched on when an injector is protruding into the needle cutting device for cutting a needle of the injector. In one example, the housing 1 and the cutter assembly 2 are both arranged within the shell body 50 of the outer shell 5. The switch 61 can be arranged in any suitable position relative to the shell body 50 of the outer shell 5. For example, the switch 61 can be arranged at the first end of the outer shell or arranged between the first end of the outer shell 5 and the second end of the outer shell 5. The switch 61 can be a mechanical flip switch or an electronic switch that is activated upon a signal that has been sensed, e.g. an optical sensor, magnetic sensor, and/or acoustic sensor. For example, the switch 61 comprises a flipping arm extending into the space between the inner surface of the shell body 50 of the outer shell 5 and the outer surface of the housing 1. Alternatively, the switch comprises an emitter and a receiver. The emitter is configured to emit a light beam or an acoustic wave towards the space between the inner surface of the shell body of the outer shell and the outer surface of the housing. The receiver is configured to receive a reflected light or acoustic signal and switch on the switch in response to a change of the receiving the reflected light or acoustic signal, so that if the object moves, or positions on the light beam or a path the acoustic signal will pass though, the reflection signal will change and thus the switch can be switched on when such change of signal is received by the receiver.

The set of electronics 6 is configured to perform, once the switch 61 is switched on, at least one action of: providing a visual, and/or an audible, and/or a tactile indication; recording data, sensing a physical property related to the injector, and reading a data from a data medium; and transmitting data.

The set of electronics may comprise at least one of an energy source 62, a communication unit 63, a clock, a processor, an indication unit and a recording unit, e.g. ROM and/or RAM. The energy source can be a portable battery or a wireless or wire-connected power supply. The communication unit can be a wire-connected communication port or a wireless communication unit, e.g. GPRS, LTE, 3G, 4G, 5G, WiFi, LPWAN, Bluetooth, Zigbee, RFID, or NFC. The indication unit can be at least one of an LED, a display, a buzzer, a speaker, and a vibration motor.

In another example, the needle cutting device comprises a partition 7 positioned between the set of electronics and the housing 1. In this example, an aperture 71 is arranged on the partition 7 and lined up to the switch 61 of the set of electronics 6, so that an inserted injector will not accidentally damage the set of electronics 6.

FIGS. 7A-8D illustrate an operation sequence of the needle cutting device upon cutting a needle from an auto-injector M. The auto-injector comprises a needle guard G. The auto-injector is first inserted into the needle cutting device from the first end of the outer shell 5 and the first open end 11 of the housing 1. As shown in FIG. 7C, the housing 1 is in the needle guard G of the auto-injector M, and the auto-injector is configured to switch on the switch 61. The cutter assembly 2 is configured to be pressed towards the second end 12 of the housing 1 (as shown by arrow A) by a syringe nozzle or a front shoulder portion of the syringe. Therefore, the cutter assembly is moved into the cavity of the housing 1, and the wall of the housing pushes the blade support portion in the radial direction relative to the longitudinal axis L so that the blade 22*a*, 22*b* is moved towards the longitudinal axis L (as shown by arrow B). For example, if the needle length is short, the front shoulder portion of the syringe will contact and press on the cutter body 20 earlier than the syringe nozzle. On the other hand, if the needle length is long, the syringe nozzle will contact and press the two blades 22*a*, 22*b* earlier than the syringe nozzle. When the cutter assembly 2 is moved from its first position to the second position, as shown in FIGS. 8A-8D, the needle of the auto-injector is cut.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A needle cutting device for cutting an injector needle, the needle cutting device comprising:

a housing extending along a longitudinal axis between a first open end and a second end; and a cutter assembly aligned with the housing along the longitudinal axis, wherein the cutter assembly comprises a blade and a cutter body, wherein the cutter body comprises a blade support portion, wherein the blade support portion is movable in a radial direction relative to the longitudinal axis, wherein the blade extends from the blade support portion of the cutter body towards the longitudinal axis, wherein the housing comprises a wall that defines a cavity, the cavity extending between the first open end of the housing and the second end of the housing, and wherein the blade support portion of the cutter body is wider than the cavity, so that when the cutter body is moved into the cavity, the wall of the housing pushes the blade support portion in the radial direction relative to the longitudinal axis so that the blade is moved towards the longitudinal axis.

2. The needle cutting device according to claim 1, wherein the cutter assembly is movable relative to the housing along the longitudinal axis between a first position where the cutter body is positioned out of the cavity and a second position where the cutter body is positioned in the cavity.

3. The needle cutting device according to claim 1, wherein the cutter assembly comprises a blade receiver, and wherein the blade receiver is arranged on an inner surface of the cutter body and is opposite to the blade with respect to the longitudinal axis.

4. The needle cutting device according to claim 3, wherein the blade receiver is arranged on a movable portion of the cutter body, wherein the movable portion is movable in the radial direction relative to the longitudinal axis and opposite to the blade support portion, so that when the cutter body is moved into the cavity, the wall that forms the cavity pushes both the blade support portion and the movable portion towards the longitudinal axis, so that the blade and the blade receiver are moved into contact with one another or so that the blade and the blade receiver overlap one another in the direction of the longitudinal axis.

5. The needle cutting device according to claim 3, wherein the blade receiver is a second blade.

6. The needle cutting device according to claim 1, comprising a container attached to the second end of the housing, wherein the second end of the housing is an open end, wherein the container comprises an opening coaxial relative to the housing, and wherein the container is releasably attached to the second end of the housing.

7. The needle cutting device according to claim 6, wherein the container comprises a resilient valve arranged at the opening of the container, and wherein the second end of the housing is configured to at least partially protrude through the resilient valve when the container is attached to the housing.

8. The needle cutting device according to claim 1, comprising an outer shell attached to the housing, wherein the outer shell extends along a longitudinal axis between a first end and a second end, wherein the outer shell comprises a shell body formed between the first end and the second end, a first opening at the first end, and a second opening at the second end, wherein the shell body of the outer shell is configured to at least partially surround the housing, and wherein an inner surface of the shell body of the outer shell is spaced apart from an outer surface of the housing.

9. The needle cutting device according to claim 8, further comprising:

a set of electronics arranged within the shell body of the outer shell, wherein the set of electronics comprises a switch configured to be switched on upon detection of movement relative to the switch in a space between the inner surface of the shell body of the outer shell and the outer surface of the housing.

10. The needle cutting device according to claim 9, further comprising:

a partition positioned between the set of electronics and the housing, wherein an aperture is arranged in the partition and is lined up with the switch of the set of electronics.

11. The needle cutting device according to claim 9, wherein the set of electronics is configured to perform, when the switch is switched on, at least one action of: providing a visual, an audible, and/or a tactile indication, recording data, sensing a physical property related to an injector, reading a data from a data medium, and transmitting data.

12. The needle cutting device according to claim 8, wherein the housing is indirectly attached to the container through an attachment between the outer shell and the container.

13. The needle cutting device according to claim 1, wherein the housing is sized to fit into a needle guard of an injector.

14. The needle cutting device according to claim 1, wherein the needle cutting device comprises a biasing member configured to bias the cutter body out of the cavity of the housing.

15. The needle cutting device according to claim 14, wherein the cutter body comprises a support surface facing towards the second end of the housing, wherein the housing comprises a counter support surface facing towards the first end of the housing, and wherein the biasing member adjacent to the support surface of the cutter body at one end, and adjacent to the counter surface of the housing at the other end.

* * * * *